United States Patent
Hayman et al.

(10) Patent No.: US 8,596,277 B2
(45) Date of Patent: Dec. 3, 2013

(54) TRACHEAL TUBE WITH LUMEN FOR TRACHEAL PRESSURE MEASUREMENT AND TECHNIQUE FOR USING THE SAME

(75) Inventors: Sarah Hayman, Boulder, CO (US); Alonzo Baker, Valencia, CA (US); Lockett E. Wood, Lyons, CO (US)

(73) Assignee: Covidien LP, Mansfield, MA (US)

( * ) Notice: Subject to any disclaimer, the term of this patent is extended or adjusted under 35 U.S.C. 154(b) by 932 days.

(21) Appl. No.: 12/486,869

(22) Filed: Jun. 18, 2009

(65) Prior Publication Data
US 2010/0319703 A1    Dec. 23, 2010

(51) Int. Cl.
*A61M 16/00*    (2006.01)

(52) U.S. Cl.
USPC ............ 128/207.15; 128/207.14; 128/207.16; 128/207.17; 128/200.26

(58) Field of Classification Search
USPC .................... 128/207.14–207.17, 200.26
See application file for complete search history.

(56) References Cited

U.S. PATENT DOCUMENTS

| | | | |
|---|---|---|---|
| 3,931,822 A | 1/1976 | Marici | |
| 4,285,340 A | 8/1981 | Gezari et al. | |
| 4,526,196 A | 7/1985 | Pistillo | |
| 4,552,558 A | 11/1985 | Muto | |
| 4,565,194 A | 1/1986 | Weerda et al. | |
| 4,630,606 A | 12/1986 | Weerda et al. | |
| 4,813,431 A * | 3/1989 | Brown ........................ 600/561 |
| 4,850,371 A | 7/1989 | Broadhurst et al. | |
| 4,898,168 A | 2/1990 | Yule | |
| 5,056,515 A * | 10/1991 | Abel ........................ 128/207.15 |
| 5,218,970 A | 6/1993 | Turnbull et al. | |
| 5,235,973 A | 8/1993 | Levinson | |
| 5,285,778 A | 2/1994 | Mackin | |
| 5,291,882 A | 3/1994 | Makhoul et al. | |
| 5,361,753 A | 11/1994 | Pothmann et al. | |
| 5,546,935 A | 8/1996 | Champeau | |
| 5,591,130 A | 1/1997 | Denton | |
| 5,740,796 A | 4/1998 | Skog | |
| 5,752,921 A | 5/1998 | Orr | |
| 5,819,723 A | 10/1998 | Joseph | |
| 5,885,248 A | 3/1999 | Denton | |
| 5,906,204 A | 5/1999 | Beran et al. | |

(Continued)

FOREIGN PATENT DOCUMENTS

| | | |
|---|---|---|
| DE | 19951578 | 4/2001 |
| EP | 0850652 | 7/1998 |

(Continued)

OTHER PUBLICATIONS

Lomholt, N., A Device for Measuring the Lateral Wall Cuff Pressure of Endotracheal Tubes, Acta Anaesthesiologica Scandinavica, Dec. 1992, pp. 775-778, Issue 36.

(Continued)

*Primary Examiner* — Elizabeth Houston
*Assistant Examiner* — Aundria Hairell
(74) *Attorney, Agent, or Firm* — Fletcher Yoder PC (57) ABSTRACT

According to various embodiments, a tracheal tube may include a pressure monitoring lumen configured to sample the gases in the tracheal space. The pressure monitoring lumen may be in fluid communication with a pressure transducer that provides pressure measurements. An opening of the lumen may be covered with a porous membrane that allow gas to diffuse freely in and out of the lumen, but that prevents secretions from clogging the lumen.

20 Claims, 4 Drawing Sheets

(56) References Cited

U.S. PATENT DOCUMENTS

| | | | |
|---|---|---|---|
| 6,135,111 A * | 10/2000 | Mongeon | 128/207.15 |
| 6,315,739 B1 | 11/2001 | Merilainen et al. | |
| 6,530,898 B1 | 3/2003 | Nimkar et al. | |
| 6,647,984 B1 | 11/2003 | O'Dea | |
| 6,814,077 B1 * | 11/2004 | Eistert | 128/207.14 |
| 6,820,618 B2 | 11/2004 | Banner et al. | |
| 2004/0000314 A1 | 1/2004 | Angel | |
| 2005/0279360 A1 | 12/2005 | Wei | |
| 2008/0210235 A1 | 9/2008 | Field et al. | |
| 2009/0038620 A1 | 2/2009 | Efrati | |
| 2011/0087123 A9 * | 4/2011 | Choncholas et al. | 600/538 |

FOREIGN PATENT DOCUMENTS

| | | |
|---|---|---|
| WO | 9422518 | 10/1994 |
| WO | WO 2007023492 A2 * | 3/2007 |
| WO | 2008039412 | 4/2008 |

OTHER PUBLICATIONS

Pollard, Richard. J. MD et al., Endotracheal Tube Location Verified Reliably by Cuff Palpation, Anesthesia and Analgesia, 1995, pp. 135-138.

Cardoso, Monica M. S. C. MD et al., Portable Devices Used to Detect Endotracheal Intubation During Emergency Situations: A Review, Critical Care Medicine, May 1998, pp. 957-964, vol. 26, Issue 5.

Guttmann, Josef PhD et al., Continuous Calculation of Intratracheal Pressure in the Presence of Pediatric Endotracheal Tubes, Critical Care Medicine, Apr. 2000, pp. 1-21, vol. 28, Issue 4.

Karasawa, Fujio. MD et al., Profile Soft-Seal Cuff, a New Endotracheal Tube, Effectively Inhibits an Increase in the Cuff Pressure through High Compliance Rather than Low Diffusion of Nitrous Oxide, Anesthesia and Analgesia, Dec. 2001, pp. 140-144, Issue 92.

Sondergaard, Soren. et al., Direct Measurement of Intratracheal Pressure in Pediatric Respiratory Monitoring, Pediatric Research, Dec. 2002, vol. 51, No. 3.

Dullenkopf, A. et al., Air Leakage Around Endotracheal Tube Cuffs, European Journal of Anaesthesiology, Dec. 2004, pp. 448-453, Issue 21.

Horisberger, T. et al., Measurement of Tracheal Wall Pressure: A Comparison of Three Different in Vitro Techniques, Journal of the Association of Anaesthetists of Great Britain and Ireland, Dec. 2008, pp. 418-422, Issue 63.

Khazin, Vadim MD et al., Gastroesophageal Regurgitation during Anesthesia and Controlled Ventilation with Six Airway Devices, Journal of Clinical Anesthesia, Dec. 2008, pp. 508-513, Issue 20.

Orr, Joseph A., Tracheal Pressure Controller for Ventilators, National Institute Of Allergy And Infectious Diseases, Jun. 2010, pp. 1-7.

* cited by examiner

TRACHEAL TUBE WITH LUMEN FOR TRACHEAL PRESSURE MEASUREMENT AND TECHNIQUE FOR USING THE SAME

BACKGROUND

The present disclosure relates generally to medical devices and, more particularly, to airway devices, such as tracheal tubes.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea. Such tracheal tubes may include endotracheal (ET) tubes, tracheotomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

To seal these types of tracheal tubes, an inflatable cuff may be associated with the tubes. When inflated, the cuff generally expands into the surrounding trachea to seal the tracheal passage around the tube to facilitate the controlled delivery of gases via a medical device (e.g., through the tube). For intubated patients, the flow rate and volume of gas transferred into the lungs, which may vary according to the condition of each patient, may be controlled by the settings of a ventilator. One factor that is used to determine the ventilator settings may be an airway pressure measurement, which is typically obtaining by measuring the pressure along the breathing circuit (e.g., medical tubing connecting the tracheal tube to the ventilator) at a point outside the patient. Airway pressure measured in the breathing circuit at a point outside the patient may be a useful surrogate for the pressure in the lungs, which may in turn be used for calculating a number of ventilator settings, for example settings involving pressure limits.

However, in circumstances where the internal diameter of the tracheal tube is diminished, for example through the buildup of mucosal secretions that may partially block the airflow passage of the tracheal tube, the lung pressure may be lower than the airway pressure measurement taken outside the patient. Accordingly, an airway pressure measurement may not always serve as a reliable substitute for lung pressure measurements.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Because obtaining direct measurements of the pressure in the internal space of the lungs is difficult, clinicians and respiratory specialists may use surrogate measurements of pressure along various points of breathing circuit or the patient's airway to estimate the lung pressure. The lung pressure estimates may then be used to determine the efficacy of the ventilation (e.g., the dynamic intrapulmonary compliance) and, in some cases, may be used to control the settings of a ventilator, either manually or automatically, to provide a clinical benefit to the patient.

Airway pressure may be estimated by using measurements of pressure taken along various points of the breathing circuit that are proximal to the tracheal tube. For example, such measurements may be used to assess a patient's work of breathing, which may include the airway resistance during movement of air into and out of the lungs. If the work of breathing of the patient increases, clinicians may assess whether the increase is due to increased airway resistance in the patient (e.g., stiffened lung tissue, which may be related to a clinical condition) or increased resistance in the tracheal tube due to buildup of biofilms on the inner diameter of the tube. Because airway pressure measurements taken proximal to the tracheal tube may not provide information about resistance built up distally, either in the patient or in the tube, trachea pressure measurements may provide information to the clinician about airway or tube-originated resistance. Trachea pressure may refer to pressure in the airway space below the cuff or near the distal tip of the cuff. With this information, when a patient's work of breathing increases, the clinician knows if it is due a change in the diameter of the tracheal tube or a change in the patient's respiratory system. If the resistance buildup is at least in part due to the tracheal tube, he may take action to suction secretions or increase the peak inspiratory pressure to overcome the increased resistance in the tracheal tube. If the work of breathing increase is due to the patient's respiratory system, he may deliver medication to the patient or change the ventilator settings. Unrecognized tube resistance may increased the work of breathing in patients that may otherwise be healthy enough to be weaned off of the ventilator. In addition, for patients who are able to intermittently breathe on their own but still use partial ventilator assistance, a more accurate determination of the resistance in the tube may be used to determine ventilator settings (e.g., triggering breathing assistance) for such patients. Using such information may allow the clinician to more accurately assess when a patient is ready to come off of ventilator-assisted breathing.

In particular, because the internal diameter of tracheal tube may change during the time that the patient is intubated, for example through the buildup of patient secretions within the tube, measurements taken upstream of the tracheal tube in the breathing circuit may not be reliable for estimating pressure in the lungs. In certain embodiments, a measurement of tracheal pressure may be used as a surrogate for lung pressure or other pulmonary pressure measurements. The tracheal space is contiguous with the lung space, and tracheal pressure may be a more reliable measurement than measurements taken far upstream along the breathing circuit. Direct measurements may be difficult to obtain during long-term monitoring situations, because pressure transducers incorporated into the distal end of a tracheal tube may become covered in mucus or secretions, resulting in unreliable measurements.

Accordingly, the disclosed embodiments provide a more accurate and reliable method and system for determining trachea pressure by sampling the gas in the tracheal space with a pressure monitoring lumen associated with the tracheal tube. Such a pressure monitoring lumen may be open to the tracheal space and may allow airway gases to flow into the monitoring lumen so that the pressure in the monitoring lumen may equalize with the trachea pressure. Accordingly, pressure measurements taken on the gas pressure in the pressure monitoring lumen may serve as a substitute for direct measurement of pressure in the trachea.

Pressure monitoring lumens associated with tracheal tubes may be relatively narrow to prevent interfering with normal respiration through the airway path of the tube. Because these lumens are so narrow, they may become easily clogged with mucus or other secretions that are present in the patient's airway. To prevent these secretions from clogging the pressure monitoring lumen, the opening in the lumen may be protected with a porous membrane that is permeable to airway gases, but that provides a solid barrier to viscous secretions. The porous membrane may also be hydrophobic, which may discourage the relatively hydrophilic secretions from being deposited on the porous membrane.

In certain presently contemplated embodiments, the calculated trachea pressure based on the pressure in the pressure monitoring lumen may be used to evaluate, adjust, or correct airway pressure values obtained along the breathing circuit or tracheal pressure values. For example, if the estimate of trachea pressure based on pressure monitoring lumen varies significantly from the airway pressure measured upstream at a point closer to the ventilator, a clinician may be able to determine that the tracheal tube is blocked with secretions or other buildup, or that some other condition has developed, which may involve action by the clinician.

In embodiments, the disclosed tracheal tubes, systems, and methods may be used in conjunction with any appropriate medical device, including without limitation a feeding tube, an endotracheal tube, a tracheotomy tube, a circuit, an airway accessory, a connector, an adapter, a filter, a humidifier, a nebulizer, nasal cannula, or a supraglottic mask/tube. The present techniques may also be used to monitor any patient benefiting from mechanical ventilation, e.g., positive pressure ventilation. Further, the devices and techniques provided herein may be used to monitor a human patient, such as a trauma victim, an intubated patient, a patient with a tracheotomy, an anesthetized patient, a cardiac arrest victim, a patient suffering from airway obstruction, or a patient suffering from respiratory failure.

Figure 1:
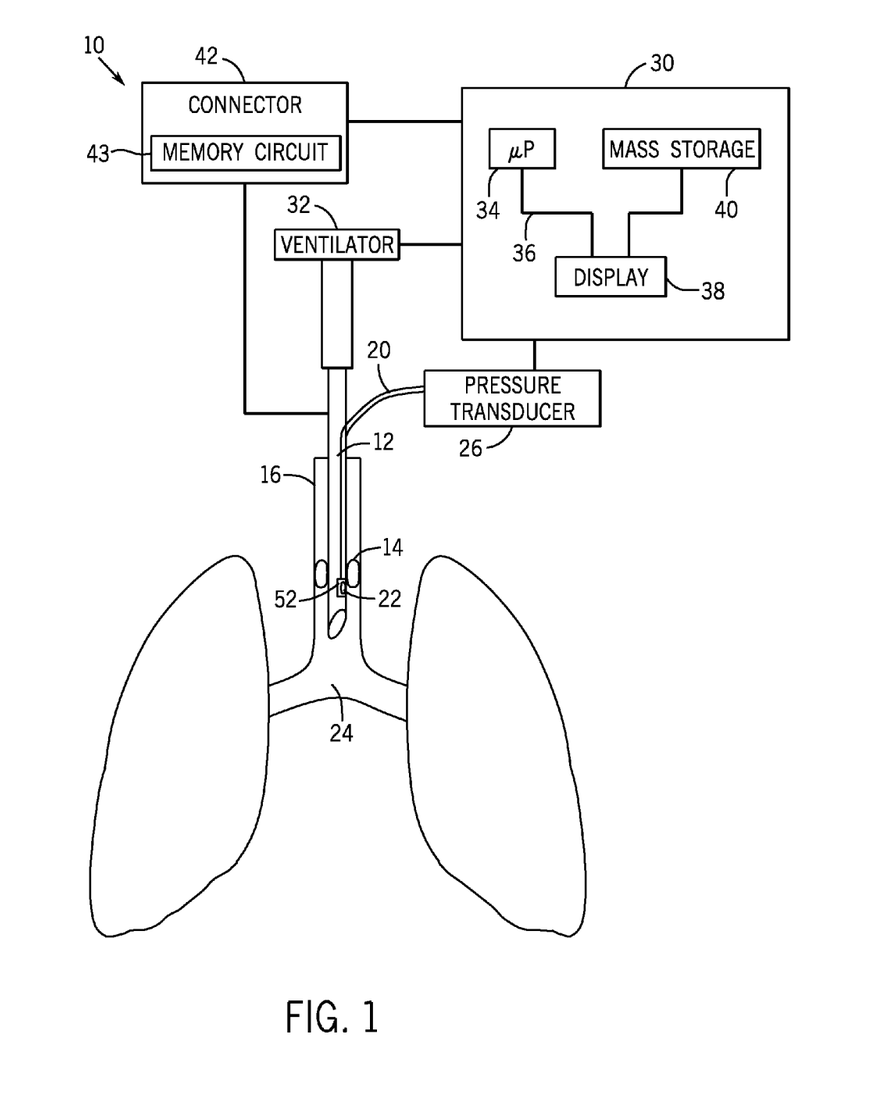
FIG. 1 illustrates a system including an endotracheal tube with a pressure transducer according to embodiments of the present techniques.

FIG. 1 shows an exemplary tracheal tube system 10 that has been inserted into a patient's trachea. The system 10 includes a tracheal tube 12, shown here as endotracheal tube, with an inflatable balloon cuff 14 that may be inflated to form a seal against tracheal walls 16. The tracheal tube 12 may also include a pressure monitoring lumen 20 that has an opening 22 at the distal end of the lumen 20 such that the lumen 20 is in fluid communication with the tracheal space 24. The opening 22 may be covered by a porous membrane, discussed below. A proximal portion of the pressure monitoring lumen may be in fluid communication with a pressure transducer 26, which in turn may communicate with a monitor 30. The pressure transducer 26 may be located outside the tracheal tube 12 or may be disposed in the lumen 20.

When the system 10 includes devices that facilitate positive pressure ventilation of a patient, such as ventilator 32, any ventilator may be used, such as those available from Nellcor Puritan Bennett LLC. As noted, the system may also include monitor 30 that may be configured to implement embodiments of the present disclosure. The monitor 30 may be a stand-alone device or may be coupled to another patient monitor or to the ventilator 32. The monitor 30 may include a microprocessor 34 coupled to an internal bus 36 and a display 38. Regardless of where it is placed, the microprocessor, or any other suitable processing circuitry, aids in computing the pressure in the pressure monitoring lumen 20. The information may then be stored in mass storage device 40, such as RAM, PROM, optical storage devices, flash memory devices, hardware storage devices, magnetic storage devices, or any suitable computer-readable storage medium. The information may be accessed and operated upon according to microprocessor 34 instructions. In certain embodiments calibration information may be used in calculations for estimating of pressure in the lungs. The monitor 30 may be configured to provide indications of the lung pressure, such as an audio, visual or other indication, or may be configured to communicate the estimated lung pressure to another device, such as the ventilator 32.

The tracheal tube 12 may also include a connector 42 that communicates with monitor 30 to provide calibration information specific to the tube 12. The connector 42 may be suitably configured to connect to a receiving port on the monitor 30. The connector 42 may contain an information element (e.g., a memory circuit 43), such as an EPROM, EEPROM, coded resistor, or flash memory device for storing calibration information for the cuff 14. The connector may also contain certain processing circuitry for at least partially processing signals from the pressure sensor or for interacting with any memory circuitry provided. When the connector 42 is coupled to the monitor 30, the information element may be accessed to provide pressure calibration information to the monitor 30. In certain embodiments, the calibration information may be provided in a barcode that may be scanned by a reader coupled to the monitor 30. Alternatively, the pressure transducer 26 may include a passive or active RFID circuit that may be read wirelessly to convey pressure monitoring information and cuff calibration information to the monitor 30. In other embodiments, tube identifying data, calibration data, and so forth may simply be entered manually.

Figure 2:
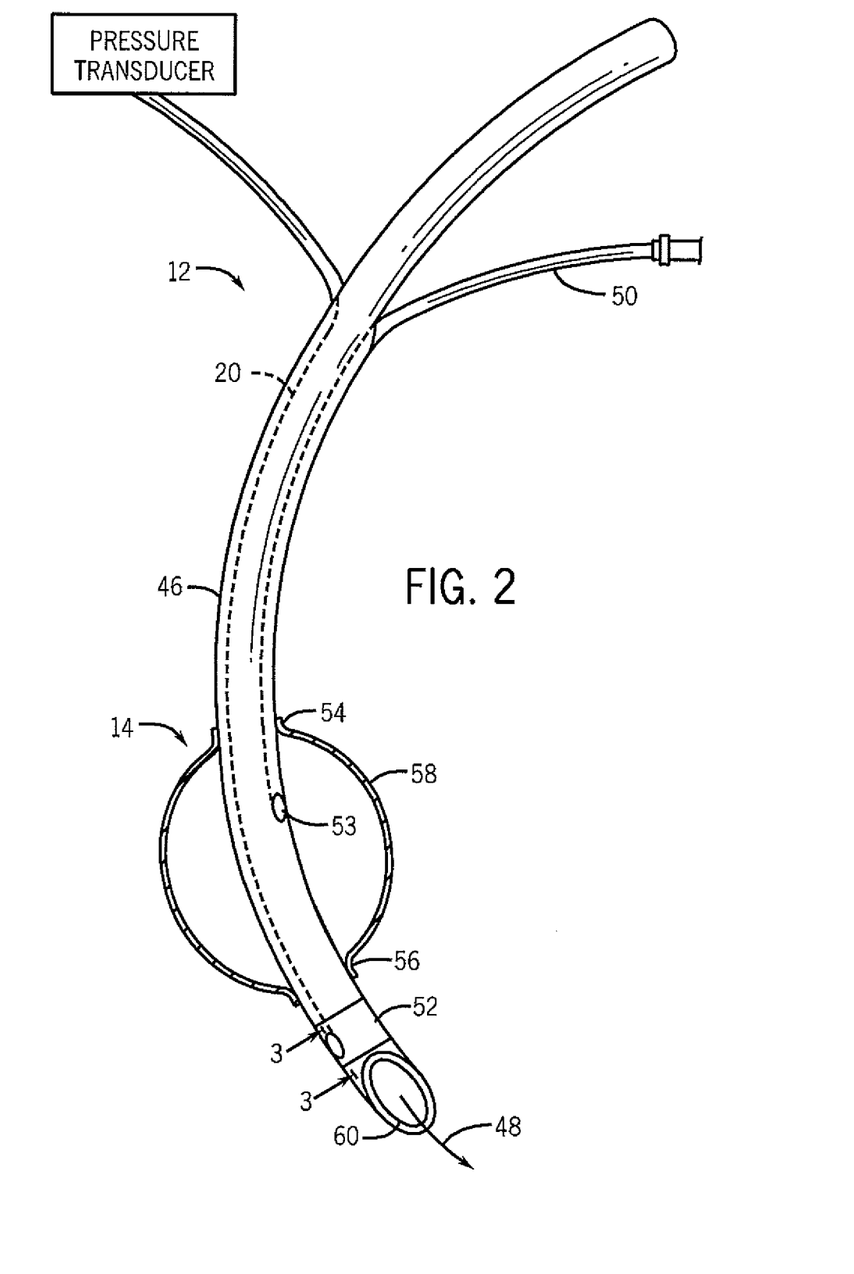
FIG. 2 is a perspective view of an endotracheal tube with a pressure monitoring lumen that may be used in conjunction with the system of FIG. 1.

FIG. 2 is a perspective view of an exemplary tracheal tube 12 according to certain embodiments. As noted, the tube 12 may include a pressure monitoring lumen 20 disposed on or in a wall 46 of the tube. The tube walls 46 define an airway flow path for delivering respiratory fluids (e.g., gases) to a patient's lungs (as shown by arrow 48) and for allowing gases to flow out of the lungs. The pressure monitoring lumen 20 may be formed in the wall of the tube and may terminate in an opening 22, which is covered by a porous membrane 52. The porous membrane 52 may be adhered or otherwise applied to the cuff walls, as discussed below. The tube 12 also includes an inflatable cuff 14, which may be inflated via a separate inflation lumen 50, which terminates in an opening 53 in the cuff walls between the adhesion points of the proximal cuff shoulder 54 and the distal cuff shoulder 56. The cuff walls 58 substantially enclose the air space around the cuff inflation opening 53, allowing the cuff 14 to be inflated when air is delivered through the inflation lumen 50.

It is contemplated that the porous membrane 52 may be suitably sized and shaped to cover the opening 22. For example, as shown, the porous membrane 52 may form a strip that is wrapped around the circumference of the tube 12 to cover the opening 22. In other embodiments, the porous membrane may be a tab that is sized only slightly larger than the opening 22. For example, an opening 22 may be 3 mm by 3 mm, so the porous membrane may be larger than about 9 mm$^2$. To adhere the porous membrane 52 to the tube 12, a portion of the tube 12 to which the membrane 52 is to be applied may be partially melted, e.g., with a heat gun, and the membrane 52 may be sealed to the melted material of the tube 12. Alternatively, the porous membrane 52 may be ultrasonically welded to the tube 12. In any case, the porous membrane 52 may be stretched across the opening 22 or may have a certain amount of slack, which may provide some strain relief to the membrane material.

The porous membrane 52 may be formed from polymeric materials such as poly (vinylidene fluoride), poly(ethyleneterephthalate), fluoropolymers such as polytetrafluoroethylene (e.g., Teflon®) polypropylene, polystyrene, polycarbonate, PVC, or nylon. In other embodiments, the porous membrane 52 may be formed by any material that fulfills the physical and/or mechanical properties as provided.

In one embodiment, the porous membrane 52 may be characterized by its degree of hydrophobicity. A hydrophobic porous membrane 52 may be advantageous, as patient secretions tend to be water-based. A hydrophobic membrane 52 may repel such secretions, preventing buildup on the membrane 52 and allowing the tracheal air to diffuse freely into the lumen 20. One measure of hydrophobicity is a contact angle measurement, done by, for example, the sessile drop method. On hydrophilic surfaces, a water droplet will spread out over a larger area than on a hydrophobic surface. The contact angle is the angle at which a liquid/vapor interface meets the solid surface. The shape of the droplet may be determined by the Young-Laplace equation. On many hydrophilic surfaces, water droplets will exhibit contact angles of 0° to 40°. For example, certain hydrogels may be so hydrophilic that water disappears on their surfaces. Such materials may be considered to have a water contact angle of zero. On hydrophobic surfaces, which are resistant to water, a large contact angle (70° to 90°) may be observed. Thus, the porous membrane 52 may have a water contact angle of greater than about 70° or greater than about 90°. It should be understood that a generally hydrophobic material, may also include hydrophobic elements, such as a hydrophilic backbone or substrate.

The porous membrane 52 may also be characterized by its mechanical and/or tensile properties. For example, the porous membrane may have pore size large enough to allow relatively rapid diffusion of tracheal gases in and out of the lumen 20. In certain embodiments, the porous membrane 52 may have pore sizes greater than 0.4 micrometers, greater than 0.5 micrometers, or greater than 1 micrometer. The porous membrane 52 may be also characterized by its breaking strength. Because pressure in the trachea rarely exceeds 60 mm H$_2$0, a material strong enough to withstand such pressures may be used for the porous membrane 52. The break strength of the porous membrane 52 may be determined by pressurizing the lumen 20 and the surrounding space to incrementally increasing pressures until a breaking point is reached.

In addition, the porous membrane 52 may include an antimicrobial agent that may protect the material from fouling during storage or that may prevent buildup on the surface. In certain embodiments, the antimicrobial agent may be a metal such as copper, silver, or gold in a metal bearing material. In embodiments, the metal may be elemental silver, powdered silver, silver ions (Ag$^+$), or a silver bearing material like silver oxide (AgO). In other embodiments, the antimicrobial agent may be an antibiotic, an antiviral, a fungicide, or other chemical agent.

Figure 3:
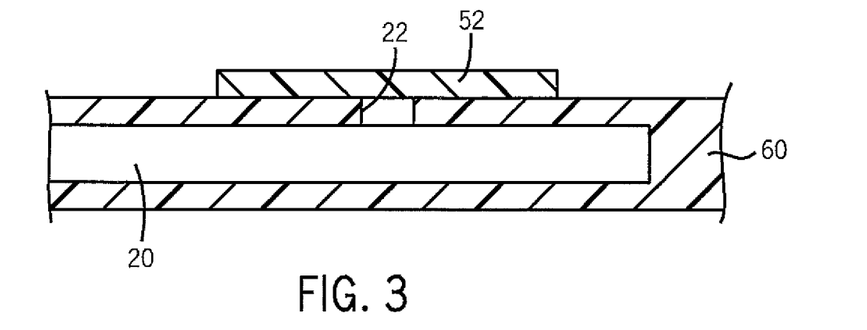
FIG. 3 is a cross-sectional view of the endotracheal along an axis of the pressure monitoring lumen.

The pressure monitoring lumen 20 may be formed within the walls 46 of the tube 12, for example by extrusion, as shown in FIG. 3, a cross-sectional view of the tube 12 along the axis of the lumen 20. The opening 22 in the tube walls 46 may be located at any position on the tube 12 distal to the distal cuff shoulder 56 to sample the gases in tracheal space 24. For example, the opening may located 1-3 mm distally of the distal cuff shoulder 56. Such a location may provide decreased exposure to secretions. Generally, the lumen 20 may be open through the most of the length of the walls 46 and may terminate at the distal end 60, where the lumen may be sealed shut, e.g., via heat-sealing. For extruded tubes 12, when the distal end 60 is cut at a slant, the distal end of the lumen 20 may be concurrently sealed. However, it is contemplated that the opening 22 may be located at the distal end 60 of the tube 12. In such an embodiment, the opening 22 may be reformed after the slant tip is cut and a porous membrane 52 may be applied directly on the slanted end to the cover the opening 22. The opening 22 may be formed by cutting or forming a notch through a portion of the wall 46. While the opening 22 may be any size, its diameter may be proportional to the diameter of the lumen 22. For example, a 1 mm lumen may have an opening 3 mm in diameter. Alternatively, the pressure monitoring lumen 20 may be a separate structure that is adhered to or otherwise associated with the tube 12 prior to insertion. In such embodiments, the opening 22 may be preformed at an appropriate location.

The tube 12 and the cuff 14 may be formed from materials having suitable mechanical properties (such as puncture resistance, pin hole resistance, tensile strength), chemical properties (such as biocompatibility). In one embodiment, the walls of the cuff 14 are made of a polyurethane having suitable mechanical and chemical properties. An example of a suitable polyurethane is Dow Pellethane® 2363-80A. In another embodiment, the walls of the cuff 14 are made of a suitable polyvinyl chloride (PVC). In one embodiment, the cuff 14 may be generally sized and shaped as a high volume, low pressure cuff that may be designed to be inflated to pressures between about 15 cm H$_2$O and 30 cm H$_2$O.

The system 10 may also include a respiratory circuit connected to the endotracheal tube 12 that allows one-way flow of expired gases away from the patient and one-way flow of inspired gases towards the patient. The respiratory circuit, including the tube 12, may include standard medical tubing made from suitable materials such as polyurethane, polyvinyl chloride (PVC), polyethylene teraphthalate (PETP), low-density polyethylene (LDPE), polypropylene, silicone, neoprene, polytetrafluoroethylene (PTFE), or polyisoprene.

Figure 4:
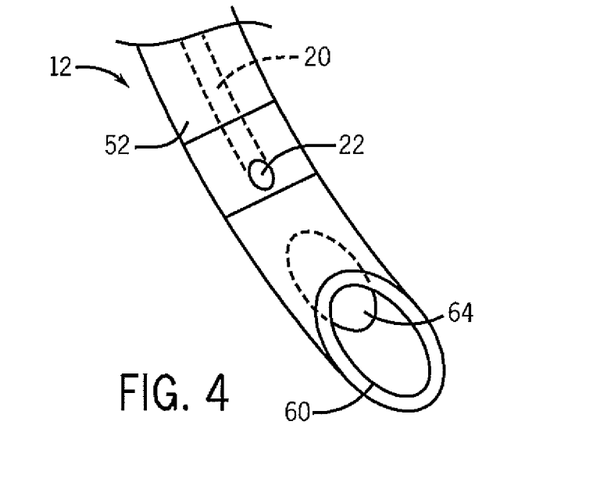
FIG. 4 is a perspective view of a distal end of the endotracheal tube.

The lumen 20 and the opening 22 may also be positioned relative to other structures on the tube 12. For example, as shown in FIG. 4, the pressure monitoring lumen 20 and opening 22 may be located opposite a Murphy eye 64, which is located near the distal end 60 of the tube 12. During operation of the tube 12, the Murphy eye 64 may become partially clogged with secretions or may become temporarily lodged against the tracheal walls. Accordingly, it may be advantageous to place the opening 22 on a side of the tube 12 away from the Murphy eye 64.

Figure 5:
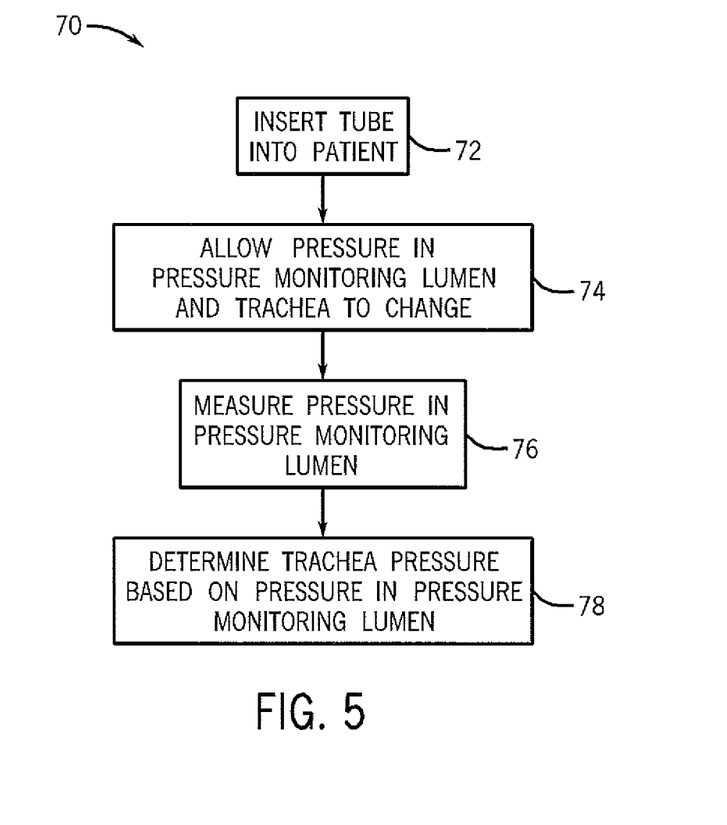
FIG. 5 is a flow diagram of an exemplary method for monitoring tracheal pressure.

FIG. 5 is a process flow diagram illustrating a method for determining tracheal pressure in conjunction with tracheal tubes and systems as provided. The method is generally indicated by reference number 70 and includes various steps or actions represented by blocks. It should be noted that the method 70 may be performed as an automated procedure by a system, such as system 10. Further, certain steps or portions of the method may be performed by separate devices. For example, a first portion of the method 70 may be performed by a caregiver, while a second portion of the method 70 may be performed by a monitor 30. In embodiments, the method 70 may be performed continuously or intermittently for long-term patient monitoring or at any appropriate interval depending on the particular situation of the intubated patient.

In certain embodiments, the method 70 begins with insertion of the tube 12 into the patient at step 72. At that point, when the tracheal space 24 is sealed, the gases in the trachea may diffuse into the monitoring lumen 20 until the pressure in the monitoring lumen 20 is substantially changed towards the pressure in the trachea at step 74. Depending on the size of the monitoring lumen 20, this may happen within milliseconds or seconds.

The time to the pressure change may be influenced by several factors. For example the time to pressure change may be influenced by the rate of gas entering the lumen. This may be influenced by the lumen length and diameter (e.g., the total volume of the lumen), the resistance of the material on the inside walls of the lumen 20, the size and shape of opening 22, the thickness and pore size of the membrane 52, the tendency of the membrane 52 to accumulate viscous buildup, and the size, shape, and resistance of any additional tubing connecting the lumen 20 to the transducer 26. Any of these may be altered to change the rate of gas entering the lumen 20. For example, a hydrophobic membrane with a larger pore size or a thinner profile may be used to accelerate the rate of diffusion into the lumen 20. In addition, a more hydrophobic membrane 52 may accumulate less buildup. The opening 22 and diameter of the lumen 22 may be changed in size and shape. Generally, any of the above factors may be altered to decrease the time response associated with the monitoring lumen 20 or the membrane 52.

Additional factors that may influence the observed time to pressure change may be the speed of the transducer 26 signal response. This may be influenced by the speed of sound as well as by a time constant related to the dead space in the transducer or other factors that modify the response of the system. The transducer time response may be known by the manufacturer of the transducer 26 and may be programmed into the monitor 30 as part of the calibration. In one embodiment, the total time response of the system may be expressed as $y(t)=h(t)*x(t)$, where $y(t)$ is the time response given the input of $x(t)$ and $h(t)$ is the transfer function that characterizes their relationship. By solving the equation in the frequency domain (e.g., via Fourier transforms or Laplace transforms), a transfer function the transducer circuit may be determined, such as $[1/(1+Ts)]$ where T is the time constant for the circuit. This implies that if an inverse transfer function of the form $(1+Ts)$ could be found, then the raw data from transducer 26 may be filtered or otherwise processed to account for the time response in the system.

In one embodiment, a transducer 26 may be selected in which the inherent response time of the transducer is suitably fast, e.g, where the time response of the transducer 26 is a minimal portion of the total time response. In cases where the transducer 26 is relatively faster or slower, the signal from the transducer 26 may be filtered or otherwise processed to account for the time response.

At step 78, a pressure transducer 26 in fluid communication with the lumen 20 may provide pressure readings to a connected device, such as a monitor 30. The monitor 30 may perform analysis of the pressure readings at step 78. In embodiments, the monitor may apply a correction factor to the pressure readings in determining the tracheal pressure. The correction factor may be determined empirically, and may be stored in the connector 42 or the monitor 30. The correction factor may account for an overall decrease in pressure readings when there is some buildup on the porous membrane 52, which may occur over time during the intubation of the patient. When the effect of buildup is small (e.g., a 4% decrease in measured pressure in the case of buildup), the correction factor may apply an overall 2% decrease to pressure readings to split the difference between cases of no buildup (a 0% change in the measured pressure) and high buildup (a 4% decrease). In addition, the correction factor may account for any time response, as provided above. The trachea pressure may be displayed or otherwise further processed to determine if the inner diameter of the tube 12 has decreased, and/or to change the settings on the ventilator 32.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of tracheal tube pressure, but these techniques may also be utilized for the measurement and/or analysis of the surrounding pressure for any medical device inserted into a patient's airway. Rather, the various embodiments may cover all modifications, equivalents, and alternatives falling within the spirit and scope of the disclosure as defined by the following appended claims.

What is claimed is:

1. A system comprising:
a tracheal tube comprising a distal end and a proximal end, wherein the tube is capable of transferring a fluid to a patient's lungs;
an inflatable cuff associated with the tracheal tube, the inflatable cuff comprising a distal shoulder and a proximal shoulder;
a lumen disposed in a wall of the tracheal tube, wherein the lumen comprises an opening in the wall of the tracheal tube between the distal shoulder of the cuff and the distal end of the tracheal tube; and
a porous membrane covering the opening, wherein the porous membrane is substantially permeable to the fluid; and
a monitor comprising:
a memory circuit storing data representative of a relationship between a secretion buildup on the porous membrane and a tracheal pressure value, wherein the data comprises a correction factor representative of an estimated secretion buildup on the porous membrane; and
a processor configured to adjust the tracheal pressure value to account for the secretion buildup based on the correction factor.

2. The system of claim 1, wherein the memory circuit stores data representative of a relationship between a pressure in the lumen and a the tracheal pressure value.

3. The system of claim 1, wherein the memory circuit is associated with a connection or cable on the tracheal tube.

4. The system of claim 1, comprising a pressure transducer in fluid communication with the lumen.

5. The system of claim 1, wherein the porous membrane comprises a hydrophobic material.

6. The system of claim 5, wherein the hydrophobic material comprises a material with a water contact angle greater than about 70 degrees.

7. The system of claim 1, wherein the porous membrane comprises a material with a break strength greater than about 60 cm $H_2O$.

8. The system of claim 1, wherein the porous membrane comprises a material with a pore size greater than about 0.4 micrometers.

9. The system of claim 1, wherein the porous membrane comprises one or more of polyvinylidene fluoride, poly(ethyleneterephthalate), or polytetrafluoroethylene.

10. The system of claim 1, wherein the porous membrane encircles at least a portion of the tracheal tube.

11. A system for determining trachea pressure comprising:
    a tracheal tube comprising a distal end and a proximal end and configured to transfer a fluid to a patient's lungs;
    a lumen disposed in a wall of the tracheal tube, wherein the lumen comprises an opening in the wall of the tracheal tube adjacent to the distal end; and
    a porous membrane covering the opening, wherein the porous membrane is substantially permeable to the fluid;
    a pressure transducer in fluid communication with the lumen; and
    a monitor comprising:
        a memory circuit storing instructions to determine a corrected trachea pressure based upon a signal from the pressure value transducer and a correction factor representative of an estimated secretion buildup on the porous membrane; and
        a processor configured to execute the instructions.

12. The system of claim 11, comprising an information element associated with the tracheal tube, wherein the information element comprises stored data representative of a relationship between a pressure in the lumen and a trachea pressure.

13. The system of claim 11, wherein the porous membrane comprises a hydrophobic material.

14. The system of claim 11, wherein the hydrophobic material comprises a material with a water contact angle greater than about 70 degrees.

15. The system of claim 11, wherein the porous membrane comprises a material with a break strength greater than about 60 cm $H_2O$.

16. The system of claim 11, wherein the porous membrane comprises a material with a pore size greater than about 0.4 micrometers.

17. The system of claim 11, wherein the porous membrane comprises one or more of polyvinylidene fluoride, poly(ethyleneterephthalate), or polytetrafluoroethylene.

18. A system comprising:
    a tracheal tube comprising a distal end and a proximal end, wherein the tracheal tube is capable of transferring a fluid to a patient's lungs;
    a lumen substantially parallel to the tracheal tube, wherein the lumen comprises an opening in the wall of the tracheal tube adjacent to the distal end; and
    a porous membrane covering the opening, wherein the porous membrane is substantially permeable to the fluid; and
    a monitor comprising:
        a memory circuit storing data representative of a relationship between a feature of the porous membrane and a tracheal pressure value, wherein the data comprises a correction factor representative of the feature on the porous membrane; and
        a processor configured to adjust the tracheal pressure value to correct for secretion buildup on the porous membrane based on the correction factor.

19. The system of claim 18, comprising a pressure transducer in fluid communication with the lumen.

20. The system of claim 19, wherein the pressure transducer is disposed in the lumen.

* * * * *